(12) United States Patent
Hartley

(10) Patent No.: US 6,894,030 B2
(45) Date of Patent: May 17, 2005

(54) TREATMENT OF DNA VIRAL INFECTIONS

(75) Inventor: Christopher Edward Hartley, Halesowen (GB)

(73) Assignee: Henderson Morley Research and Development Limited (GB)

( * ) Notice: Subject to any disclaimer, the term of this patent is extended or adjusted under 35 U.S.C. 154(b) by 80 days.

(21) Appl. No.: 10/168,945

(22) PCT Filed: Dec. 13, 2000

(86) PCT No.: PCT/GB00/04793

§ 371 (c)(1),
(2), (4) Date: Sep. 3, 2002

(87) PCT Pub. No.: WO01/49242

PCT Pub. Date: Jul. 12, 2001

(65) Prior Publication Data

US 2003/0050253 A1 Mar. 13, 2003

(30) Foreign Application Priority Data

Dec. 30, 1999 (GB) ............................................. 9930811
Jan. 12, 2000 (GB) ............................................. 0000683
Sep. 21, 2000 (GB) ............................................. 0023198

(51) Int. Cl.$^7$ ..................... A01N 43/04; A01N 43/08; A61K 31/70; A61K 31/34
(52) U.S. Cl. ......................... 514/26; 514/25; 514/27; 514/33; 514/34; 514/461; 514/471

(58) Field of Search ........................... 514/25–31, 224.2

(56) References Cited

U.S. PATENT DOCUMENTS

2002/0019443 A1 * 2/2002 Campbell .................... 514/562

FOREIGN PATENT DOCUMENTS

| EP | 442744 A2 | * | 8/1991 |
| EP | 0 442 744 A | | 8/1991 |
| WO | WO 00/10574 | * | 3/2000 |

OTHER PUBLICATIONS

Manunta et al., "Structure–Activity Relationships for the Hypertensinogenic Activity of Ouabain", Hypertension, 37[part 2], pp. 472–477, 2001.*

T.G. Voss, "Reduction of Human Immunodeficiency Virus Production and Cytopathiceffects by Inhibitors of the NA+/K+/Cl—Cotransporter", Virology, Academic Press, Orlando, US, vol. 219, No. 249, 1996, pp. 291–294, XP002925373, ISSN: 0042–6822.

* cited by examiner

Primary Examiner—James O. Wilson
Assistant Examiner—Traviss C. McIntosh, III
(74) Attorney, Agent, or Firm—Caesar, Rivise, Bernstein, Cohen & Pokotilow, Ltd.

(57) ABSTRACT

The synergistic combination of a loop diuretic and a cardiac glycoside is useful in the treatment of DNA viral infections.

7 Claims, No Drawings

TREATMENT OF DNA VIRAL INFECTIONS

The invention relates to anti-viral treatments and in particular to prophylactic and therapeutic treatments of DNA viral infections such as Herpes virus infections.

Herpes viruses are DNA viruses, having a central core of DNA within a proteinaceous structure. DNA carries the genetic code to reproduce the virus. Viruses must infect a living cell to reproduce. There are numerous viral proteins that are well characterised including important enzymes which act as ideal targets for antiviral chemotherapy. These include DNA polymerase and thymidine kinase which are needed for DNA replication. The replication of viral DNA is essential for virus infectivity. It is known that infecting viruses can alter the natural ionic balances of a living cell in the course of their replication.

EP-A-0442 744 discloses the use of certain glycosides to treat Herpes Simplex Virus and Varicelia Zoster Virus. W0 00/10574 published after the date of the priority applications for this PCT application discloses the use of a loop diuretic in the treatment of a retrovirus, in this case to treat HIV infection. We have now unexpectedly discovered that the combined application of a glycoside and a loop diuretic gives an enhanced effect as compared to the administration of a loop diuretic or a glycoside alone.

According to the invention in one aspect there is provided a therapeutic composition useful in the treatment of viral infections comprising a synergistic combination of a loop diuretic and a cardiac glycoside.

In another aspect the invention provides a method of treating a viral infection comprising the application of a loop diuretic and a cardiac glycoside to exert a synergistic effect.

The loop diuretic may be selected from a wide range of available agents. Preferably the loop diuretic is any one or more of frusemide, bumetanide, ethacrynic acid or torasemide. According to our studies loop diuretics mediate their antiviral effects through alteration to the cellular concentration of ions, cellular ionic balances, cellular ionic milieu and electrical potentials.

Frusemide is an anthrilic acid derivative, chemically 4-chloro-N-furfuryl-5-sulfamoylanthranilic acid. It is practically insoluble in water at neutral pH, however is freely soluble in alkali. Frusemide exerts its physiological effect by inhibition of the transport of chloride ions across cell members. Frusemide is a loop diuretic with a short duration of action. It is used for treating oedema due to hepatic, renal, or cardiac failure and treating hypertension. The bioavailability of frusemide is between 60% to 70% and it is primarily excreted by filtration and secretion as unchanged drug. Frusemide acts on the Na+/K+/2Cl-cotransformer. For its diuretic effect, its predominant action is in the ascending limb of the loop of Henle in the kidney. Loop diuretics markedly promote $K^+$ excretion, leaving cells depleted in intracellular potassium. This may lead to the most significant complication of long term systemic frusemide usage namely a lowered serum potassium. We postulate that it is this action which makes loop diuretics useful as an agent against DNA viruses.

Recent evidence suggests that the major biotransformation product of frusemide is a glucuronide. Frusemide is extensively bound to plasma proteins, mainly albumin. Plasma concentrations ranging from 1 to 400 mcg/ml are 91–99% bound in healthy individuals. The unbound fraction ranges between 2.3–4.1% at therapeutic concentrations. The terminal half life of frusemide is approximately 2 hours, and it is predominantly excreted in the urine.

The cardiac glycosides may be any one or more of digoxin, digitoxin, medigoxin, lanatoside C, proscillaridin, k strophanthin, peruvoside and ouabain. Plants of the digitalis species (e.g. digitalis purpura, digitalis lanata) contain cardiac glycosides such as digoxin and digitoxin which are known collectively as digitalis. Other plants contain cardiac glycosides which are chemically related to the digitalis glycosides and these are often also referred to as digitalis. Thus the term digitalis is used to designate the whole group of glycosides; the glycosides are composed of two components a sugar and a cardenolide. Ouabain is derived from an African plant Strophanthus gratus (also known as strophanthidin G) and is available in intravenous form (it is not absorbed orally) and is used for many laboratory experiments in the study of glycosides, because of its greater solubility. It has a virtually identical mode of action as digoxin.

Digoxin is described chemically as (3b, 5b, 12b)-3-[0-2,6-dideoxy-b-D-riob-hexopyranosyl-(1"4)-O-2,6-dideoxy-b-D-ribo-hexopyranosyl-(1"4)-2,6-dideoxy-b-D-ribo-hexopyranosyl) oxy]-12,14-dihydroxy-card-20-22)-enolide. Its molecular formula is $C_{41}H_{64}O_{14}$, and its molecular weight is 780.95. Dixogin exists as odourless white crystals that melt with decomposition above 230° C. The drug is practically insoluble in water and in ether; slightly soluble in diluted (50%) alcohol and in chloroform; and freely soluble in pyridine.

Because some patients may be particularly susceptible to side effects with digoxin, the dosage of the drug should always be selected carefully and adjusted as the clinical condition of the patient warrants.

At the cellular level digitalis exerts it main effect by the inhibition of the sodium transport enzyme sodium potassium adenosine triphosphatase (Na/K ATPase); this is directly responsible for the electrophysiological effects of heart muscle and according to our understanding also its activity against DNA viruses. This activity also has an effect on the efficiency of myocardial contractility due to secondary changes in intracellular calcium. At very low intracellular concentrations of digitalis, the opposite effects can be seen with a reduced efficiency of cardiac contractions as the digitalis stimulates the Na/K ATPase.

A preferred combination is the loop diuretic frusemide and the cardiac glycoside digoxin. It is preferred that concentrations are frusemide 1 mg/ml and digoxin 30 mcg/ml. It is within the scope of the invention to separate the application of the two active ingredients by a short time period.

Studies (including X-ray microanalysis) have demonstrated the anti-viral DNA effects of a composition of the invention are dependent on a depletion of intracellular potassium ions. Briefly these studies demonstrate:

replacement of potassium will restore DNA synthesis;
  use of frusemide and digoxin in combination have comparable effects to potassium depletion;
  the level of potassium depletion is sufficient to allow normal cell function;
  the potassium depletion has no cytotoxic effects.

Thus, by altering the cellular concentrations of ions, cellular ionic balances, cellular ionic milieu and cellular electrical potentials by the application of a loop diuretic and a cardiac glycoside it is possible to change the metabolism of the cell without detriment to the cell but so that virus replication is inhibited. Accordingly, we are confirmed in the view that the use of a loop diuretic and a cardiac glycoside is of benefit in preventing or controlling virus replication by inhibiting the replication of viral DNA. Anti-viral efficacy has been demonstrated against the DNA viruses HSV1 and HSV2, CMV, VZV, and Pseudorabies. Other candidate viruses are parvoviruses; papoviruses; adenoviruses; hepadnoviruses and poxviruses.

The compositions of the invention may be adapted for external or internal administration. Topical and systemic applications are likely to be the most useful. The formulations may be adapted for slow release. It is a much preferred feature of the invention that the compositions are formulated for topical application. Other ingredients may be present, provided that they do not compromise the anti-viral activity: an example is a preservative. Preferably the invention provides a combination of frusemide and digoxin as a topical application in a buffered saline formulation for the treatment of corneal eye infections. So far as we are aware, the combination of existing. licensed compounds, for the treatment of viral infections is without precedent.

A preferred application of this invention is the use of local concentrations of loop diuretic and cardiac glycoside for the highly effective treatment of virus infections of the eye. Recurrent Herpes infections of the cornea in man is the most common viral cause of blindness.

The use of contact lenses carrying e.g. impregnated with a loop diuretic and a cardiac glycoside would be a safe and efficient method for creating high intracellular concentrations to prevent or treat the disease. A depot application of a loop diuretic and cardiac glycoside applied intra-occularly would be a suitable method for the treatment of cytomegalovirus retinitis, a major cause of blindness in patients suffering with AIDS.

The invention will now be described by way of illustration only with reference to the following examples.

EXAMPLE 1

Bioassays with herpes simplex virus in vitro were undertaken to follow the anti-viral activity of the simultaneous administration of frusemide (1 mg/ml) and digoxin (30 mcg/ml). Culture and assay methods follow those described by Lennette and Schmidt (1979) for herpes simplex virus and Vero cells with minor modifications.

Herpes Simplex Strains Used:

Type 1 herpes simplex strain HFEM is a derivative of the Rockerfeller strain HF (Wildy 1955), and Type 2 herpes simplex strain 3345, a penile isolate (Skinner et al 1977) were used as prototype strains. These prototypes were stored at −80° C. until needed.

Cell Cultures:

African Green Monkey kidney cells (vero) were obtained from the National Institute of Biological Standards and Control UK and were used as the only cell line for all experiments in the examples.

Culture Media:

Cells and viruses were maintained on Glasgows modified medium supplemented with 10% foetal bovine serum.

Results:

Inhibition of hsv1

| Multiplicity of infection (dose of virus) | Effect of frusemide alone | Effect of digoxin alone | Effect of frusemide and digoxin in combination |
|---|---|---|---|
| High | − | − | +++ |
| Medium | + | + | ++++ |
| Low | + | ++ | ++++ |

This example demonstrates that virus activity was almost eliminated by applying low concentrations of the stock frusemide and glycoside solution to Vero cells infected with hsv1. At higher concentrations virus activity was completely prevented. The anti-viral effects of this stock solution were far greater than the effects of frusemide or digoxin alone. There was no direct virucidal activity on extracellular virus.

These experiments were repeated using a hsv2 strain, and almost identical results were obtained.

EXAMPLE 2

The method of Example 1 was repeated using type 1 herpes virus strain kos. Similar results were obtained.

EXAMPLE 3

In vitro bioassays were undertaken to follow the anti-viral activity of frusemide and digoxin when applied both simultaneously and alone.

The compositions were applied to different types of vero cells (African green monkey kidney cells and BHK1 cells) and infected with type 2 herpes simplex virus (strains 3345 and 180) at low, intermediate, and high multiplicities of infection (MOI). Inhibition of virus replication was scored on the scale:

| | |
|---|---|
| no inhibition | − |
| 20% inhibition | + |
| 40% inhibition | ++ |
| 60% inhibition | +++ |
| 80% inhibition | ++++ |
| 100% inhibition | +++++ |
| T denotes drug toxicity. | |

The following results were obtained using African green monkey kidney cells and type 2 herpes simplex strain 3345:

| | Frusemide 0 mg/ml | Frusemide 0.5 mg/ml | Frusemide 1.0 mg/ml | Frusemide 2 mg/ml |
|---|---|---|---|---|
| LOW MOI HSV2 | | | | |
| Digoxin 0 mcg/ml | − | + | +++ | T |
| Digoxin 15 mcg/ml | − | + | +++ | T |
| Digoxin 30 mcg/ml | +++ | +++ | +++++ | T |
| Digoxin 45 mcg/ml | T | T | T | T |
| INT. MOI HSV2 | | | | |
| Digoxin 0 mcg/ml | − | + | +++ | T |
| Digoxin 15 mcg/ml | − | + | +++ | T |
| Digoxin 30 mcg/ml | + | ++ | +++++ | T |
| Digoxin 45 mcg/ml | T | T | T | T |
| HIGH MOI HSV2 | | | | |
| Digoxin 0 mcg/ml | − | − | ++ | T |
| Digoxin 15 mcg/ml | − | − | +++ | T |
| Digoxin 30 mcg/ml | − | − | +++++ | T |
| Digoxin 45 mcg/ml | T | T | T | T |

The greatest effect of digoxin alone (+++) occurred on application of 30 mcg/ml digoxin at low multiplicity of infection only.

The greatest effect of frusemide alone (+++) occurred on application of 1 mg/ml frusemide at low and intermediate multiplicities of infection.

When the loop diuretic and cardiac glycoside were simultaneously applied to the infected cells, the greatest effect (+++++) was achieved using digoxin at 30 mcg/ml and frusemide at 1 mg/ml. 100% inhibition of hsv2 replication was shown at low, intermediate and high multiplicities of infection.

Similar results were obtained using other combinations of vero cells and type 2 herpes simplex strains.

This example demonstrates that replication of hsv2 is not maximally inhibited by applying frusemide or digoxin alone. However, in combination frusemide and digoxin completely inhibited hsv2 replication.

What is claimed is:

1. A method of treating DNA viral infections by administering to a patient a therapeutically effective amount of frusemide and digoxin.

2. A pharmaceutical composition for treating DNA virus infections comprising a synergistic combination of frusemide and digoxin.

3. The composition of claim 2 additionally comprising a carrier material suitable for topical application of the composition.

4. The composition of claim 2 additionally comprising a carrier material suitable for systemic application of the composition.

5. The composition of claim 1 additionally comprising a carrier material suitable for intra-ocular depot application of the composition.

6. The composition of claim 1 comprising about 1 mg/ml of frusemide and about 30 mg/ml. of digoxin.

7. A contact lens impregnated with frusemide and digoxin.

* * * * *